United States Patent [19]

Lingwood

[11] Patent Number: 4,767,720
[45] Date of Patent: Aug. 30, 1988

[54] ANTIDIGOXIN ANTIBODIES

[75] Inventor: Clifford A. Lingwood, Toronto, Canada

[73] Assignee: HSC Research Development Corporation, Toronto, Canada

[21] Appl. No.: 774,370

[22] Filed: Sep. 10, 1985

[51] Int. Cl.⁴ .................. G01N 33/534; G01N 33/566
[52] U.S. Cl. .................................... 436/536; 436/531; 436/545; 436/546; 436/817; 436/823
[58] Field of Search ............... 436/501, 531, 536, 541, 436/545, 546, 804, 811, 817, 823; 530/807

[56] References Cited

U.S. PATENT DOCUMENTS 4,469,797  9/1984  Albarella ............................. 436/536

OTHER PUBLICATIONS

Cerceo et al, "Factors Affecting the Radioimmunoassay of Digoxin," Clinical Chemistry, vol. 18, No. 6, pp. 539–542 (1972).
Lingwood, "Production of Glycolipid Affinity Matrices by Use of Heterobifunctional Crosslinking Agents," Journal of Lipid Research, vol. 25, pp. 1010–1012 (1984).
Butler et al, "Digoxin-Specific Antibodies," Proc. of Nat'l. Acad. Sciences, USA, vol. 57, pp. 71–78 (1967).
Soldin et al, "Are Immunoassays for Digoxin Reliable!", Clinical Biochemistry, vol. 17, pp. 317–320 (1984).
Deffo et al, "Photoaffinity Labeling of the Sodium- and Potassium-Activated Adenosinetriphosphatase with a Cardiac Blycoside Containing the Photoactive Group on the C–17 Side Chain," Biochemistry, vol. 22, pp. 6303–6309 (1983).
"Digoxin Derivatives", Chem. Abst. 103: 54404y, p. 612, Aug. 19, 1985.
"Digoxin Derivatives", Chem. Abst. 104, 69120x, p. 71, 1986.

Primary Examiner—Sidney Marantz
Assistant Examiner—Richard Wagner
Attorney, Agent, or Firm—Banner, Birch, McKie & Beckett

[57] ABSTRACT

A digoxin derivative/immunogenic protein conjugate is disclosed which has the carbohydrate moiety of digoxin intact. Antibodies raised against this conjugate show minimal cross-reactivity to digoxin metabolites enabling the use as an antibody in the diagnostic analysis for digoxin when measured in the presence of its metabolites found in serum isolated from a human.

29 Claims, 6 Drawing Sheets

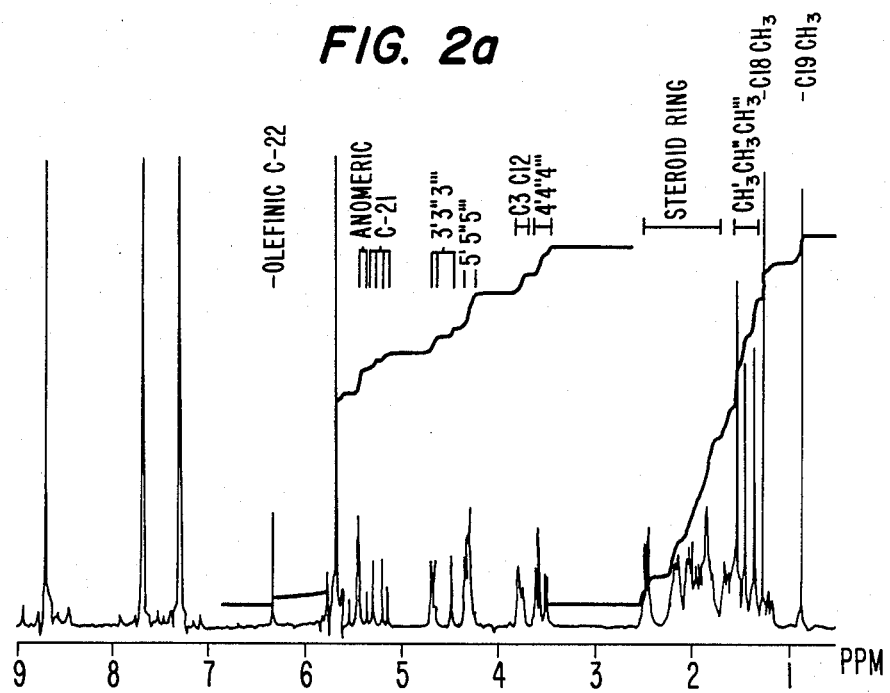
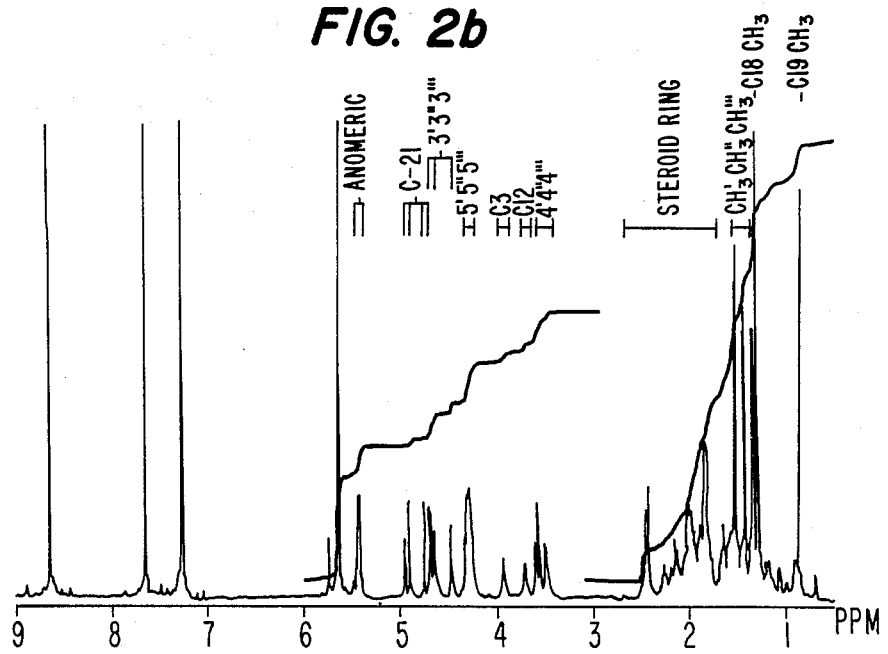

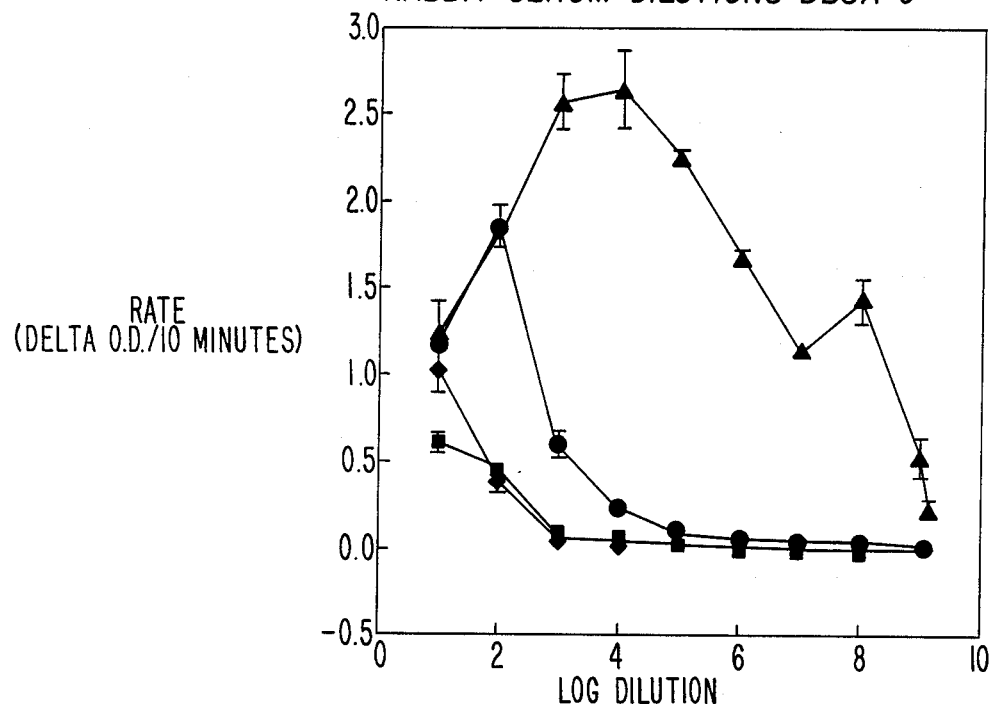
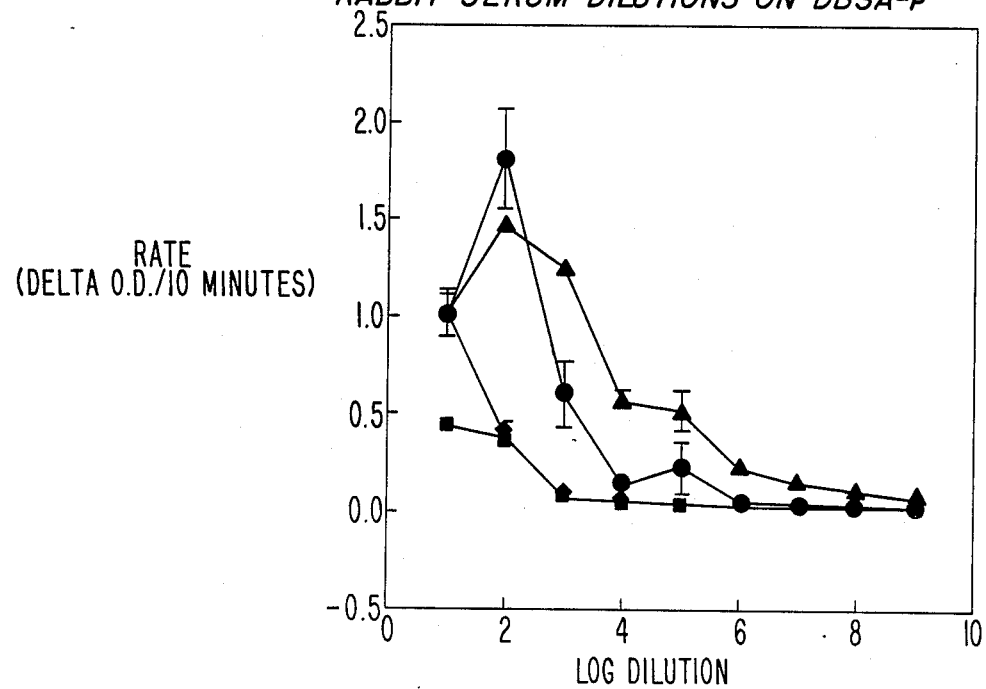

ANTIDIGOXIN ANTIBODIES

FIELD OF THE INVENTION

This invention relates to an immunoassay for digoxin in the presence of its metabolites in serum and the development of antibodies for use in such diagnostic tests.

BACKGROUND OF THE INVENTION

Digoxin is widely used in the treatment of cardiac irregularities. Efficacy of a digoxin dose, as administered to a patient, is dependent on many factors. A narrow therapeutic index necessitates an accurate and reliable means for the measurement of serum digoxin concentration. The measurement for digoxin concentrations in the serum is complicated by the metabolites of digoxin in the serum. There is considerable variation between patients regarding the manner in which digoxin is metabolized in vivo. Digoxin is a steroid-carbohydrate conjugate. A major route of metabolism is the sequential loss of glycose units and/or saturation of the steroid lactone ring. The resulting metabolites retain various degrees of biological and toxic activities of the native digoxin. The presence of metabolites have prevented the accurate measurement of digoxin by standard radioimmunoassay techniques. Serum levels of digoxin have been routinely measured by immunoassay using an antidigoxin antibody raised against a bovine serum albumin-digoxin conjugate immunogen. As described in Butler et al, (1967) Digoxin Specific Antibodies, *Proc. Natl. Acad. Sci*, 57:71-78, the bovine serum albumin (BSA)-digoxin conjugate is prepared by periodate oxidation of the vicinal hydroxyyl groups of the terminal sugar. The generated aldehyde groups are coupled to the amino groups of BSA. Thus the conjugate linkage is through the carbohydrate moiety of digoxin. The antibodies generated in vivo against this conjugate are, therefore, for the most part directed against the steroid moiety of digoxin. Thus, the metabolites, such as digoxigenin bis and monodigitoxide and digoxigenin all react with the antibodies whilst other metabolites such as dihydrodigoxigenin and dihydrodigoxin, where the C22 carbon is reduced, show little or no cross-reactivity with the antibodies. The cross-reactivity of the metabolites of digoxin with the antidigoxin antibodies is an appreciated fact and the specifications of most commercial antidigoxin sera state the degree of cross-reactivity. It has been found that for some antisera, the carbohydrate metabolites are more potent antigens than digoxin itself, the additional carbohydrate units in some way reducing the antibody binding activity of native digoxin. As a result, there is considerable variation in the anticipated extent to which the glycosidic metabolites may account for the measured digoxin concentration in serum samples.

As reported in Soldin, S; Papanastasion-Diamand, A; Heyes, J; Lingwood, C. A. and Olley, P, (1984) Are Immonuassays for Digoxin Reliable? *Clin Biochem*, 17 317-320, a detailed study of the specificity of the radioimmune assay for digoxin reveals that, in addition to the cross-reactivity of the metabolites, some thirty additional cross-reactive, often unrelated compounds have been identified in various serums.

SUMMARY OF THE INVENTION

According to this invention, a digoxin derivative/immunogenic protein conjugate is provided which has its carbohydrate moiety intact and to which antibodies may be raised which are specific to digoxin and with which digoxin metabolites have little if any cross-reactivity. The digoxin derivatives/immunogenic protein conjugate has its lactone ring at C17 opened at a double bond between C20 and C23 of the lactone ring. An immunogenic protein is coupled to the C23 of the open lactone ring without altering the carbohydrate moiety of the digoxin derivative.

According to another aspect of the invention, the digoxin derivative/immunogenic protein conjugate is prepared by opening the double bond between C20 and C23 of the C17 lactone ring of digoxin having a carbohydrate moiety at C3. An immunogenic protein is coupled to a resultant C23 of the open lactone ring without altering the carbohydrate moiety.

Antidigoxin antibodies specific to the carbohydrate moiety of the digoxin derivative/immunogenic protein conjugate are raised and used in an immunoassay diagnostic method for detecting the presence of digoxin in a fluid sample.

According to another aspect of the invention, a process is provided for preparing a compound $3\beta$-$12\beta$-$14\beta$-trihydroxy-$5\beta$-$17\beta$(glyoxylate ester of $C_{21}$ hydroxy, $C_{20}$keto)etianic acid 3-tridigitoxoside. The compound is prepared by treating digoxin with ozone to yield an ozonide in the C17 lactone ring and reducing the ozonide to produce the compound which may be used as an intermediate in the production of a digoxin derivative/methylated bovine serum albumin conjugate.

BRIEF DESCRIPTION OF THE DRAWINGS

Preferred embodiments of the invention are shown in the drawings, wherein:

FIGS. 2a and 2b show results of the nuclear magnetic resonance analysis of the hydrolysed product of the digoxin derivative;

FIGS. 6a and 6b are graphs plotting the measurement of antidigoxin activity by enzyme linked immunosorbent assay; and FIGS. 7a and 7b are graphs showing the specificity of the antidigoxin serum.

DETAILED DESCRIPTION OF THE PREFERRED EMBODIMENTS

Figure 1:
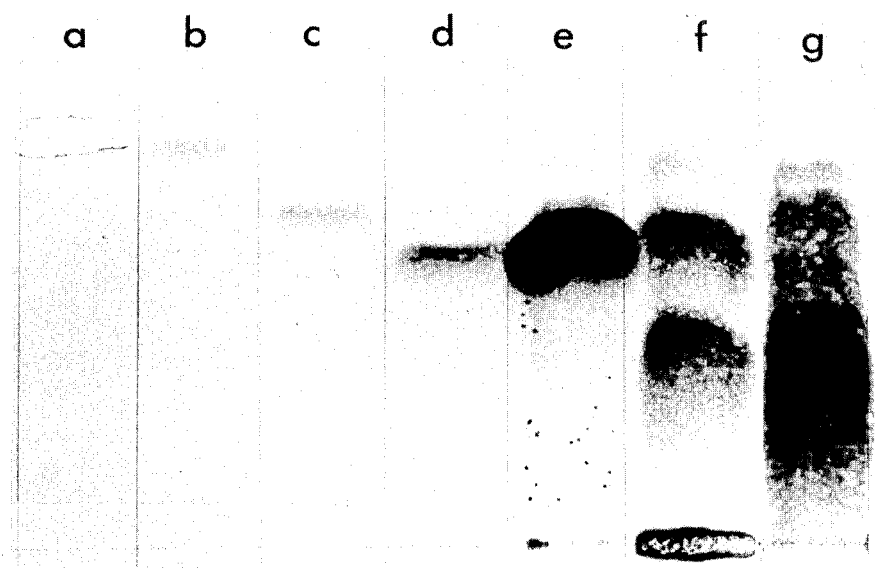
FIG. 1 shows the results of thin layered chromatography of the reaction mixture in the preparation of the digoxin derivative.

Digoxin, which can be isolated from the foxglove plant, has a carbohydrate moiety which is not found in mammals. Thus, an antibody raised against the unique carbohydrate moiety of digoxin would provide a more specific immunoassay for native digoxin. Digoxin is represented by the formula:

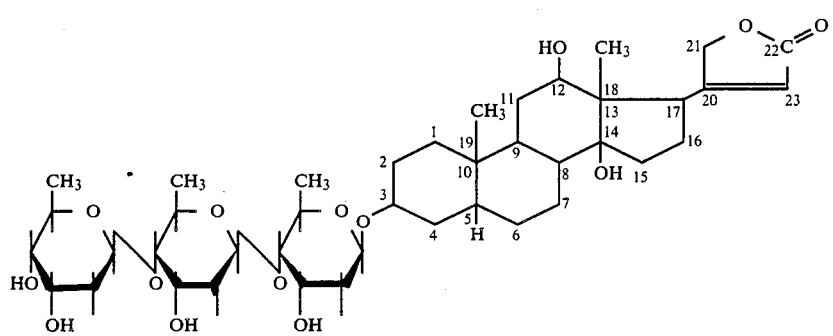

Digoxin, when metabolized in the body, produces a variety of metabolites which include digoxigenin bis-digitoxide, monodigitoxide and digoxigenin. All of these metabolites involve the modification of the carbohydrate moiety of digoxin and are the most dominant of the metabolites. Other metabolites include dihydrodigoxigenin, dihydrodigoxin and digitoxin, which involve modifications to the steroidal moiety of digoxin.

This invention is directed to the development of a digoxin derivative which is coupled to an immunogenic protein at the C23 position of the C17 lactone ring of digoxin, while leaving the carbohydrate moiety of digoxin intact. This locates the immunogenic protein on the opposite side of the steroidal moiety of digoxin to permit the raising of antibodies to the unique carbohydrate moiety and thereby provide low cross-reactivity with the metabolites of digoxin, because, as noted above, most digoxin metabolites involve the modification of the carbohydrate moiety. To achieve the coupling of the immunogenic protein to the digoxin molecule, the lactone ring is opened in a manner to provide the C23 carbon in a form which is reactive with the amine groups of the immunogenic protein. The double bond between carbon atoms C20 and C23 may be opened in accordance with a variety of organic synthesis techniques, as will be understood by those skilled in the art. According to this invention, the preferred technique is to oxidize the lactone ring to form an ozonide. The oxidation of the lactone ring may be effected by the use of ozone in ozonolysis, the use of osmium tetroxide or the use of potassium permaganate in acetone. According to the preferred embodiment of this invention, ozonolysis is used to form the ozonide as follows.

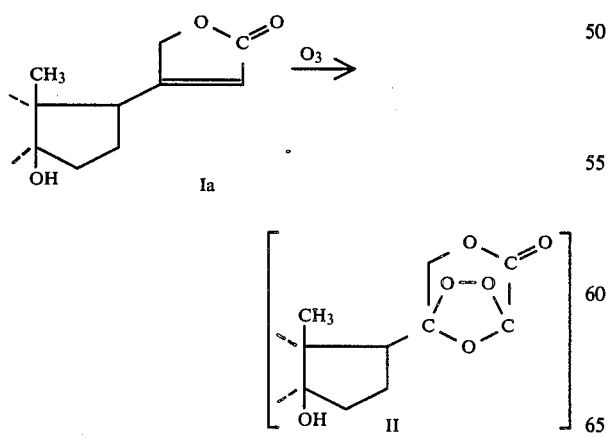

The ozonide may then be opened by reduction to produce an aldehyde at C23 or by oxidation to produce a carboxyl group at C23. It is appreciated that there are many useful forms of reductants which may be used in reducing the ozonide to open the ring, as will be appreciated by those skilled in the art. The preferred reductant is dimethylsulfide which, when reacted with the ozonide of the above formula II, results in the aldehyde of the following formula III:

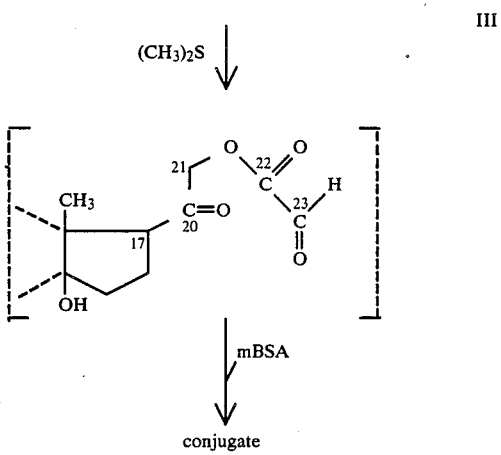

The structure of formula III, which can be identified as 3 $\beta$,12 $\beta$,14 $\beta$-trihydroxy-5 $\beta$,17$\beta$ (glyoxylate ester of $C_{21}$ hydroxy, $C_{20}$keto)etianic acid 3-tridigitoxoside is unstable where the glyoxylate radical dissociates to form glyoxylic acid. Thus to confirm that the compound of formula III is prepared when the ozonide is reduced, the reaction mixture is immediately hydrolyzed under mild basic conditions, such as by the use of the alkaline $KHCO_3$, to yield the product of the following formula:

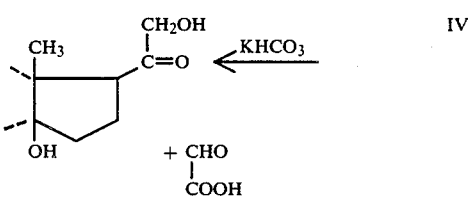

By means of nuclear magnetic resonance analysis and mass spectrometry, the digoxin derivative of formula IV is confirmed to thereby indicate that the aldehyde of formula III is prepared when the ozonide of formula II is reduced.

It is further appreciated that, instead of the preparation of the aldehyde of formula III by reduction of the ozonide of formula II, it is possible to oxidize the ozonide of formula II to produce a carboxylate at C23. The ozonide may be oxidized by use of performic acid to yield a compound of the following formula:

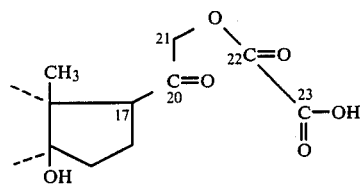

V

The immunogenic protein may be coupled to the C23 carboxylate by use of catalyst, such as dicyclocarbodiamide which catalyses the reaction of the amine groups of the protein moiety with the C23 carboxyl group of the digoxin derivative.

It is appreciated that in the field of immunology that a variety of immunogenic proteins may be coupled to the digoxin derivative to provide a conjugate which, when appropriately treated and injected into an animal, can raise antibodies to the conjugate. It is further appreciated that a diamine may be used in linking the desired immunogenic protein to the C23 carbon of the digoxin derivative of formula III or V. Such diamines include 4-aminophenylethylamine. Suitable immunogenic proteins include bovine serum ablumin (BSA) which is not soluble in an organic reaction medium which may be used in the production of the derivatives of formulas III an V. In the event that it is desired to react directly the immunogenic protein with the unstable aldehyde of formula III, the organic soluble form of BSA, namely methylated bovine serum albumin (mBSA), may be used. It has been discovered that, and in accordance with a preferred embodiment of this invention, the use of mBSA when immediately added to the reaction mixture after the reduction step, produces a conjugate having in the range of 30 up to 50 digoxin derivative molecules attached to a single mBSA molecule. The coupling of the digoxin derivatives to the mBSA results in a Schiff's base with the aldehyde of formula III. This is reduced to provide the stable conjugate which may be purified or isolated from the reaction mixture by dialysis and the like and lyophilized for use in raising antibodies in an animal.

The immunization may be conducted in accordance with standard techniques, such as injecting the conjugate subcutaneously into a rabbit at multiple sites. Booster injections may be later injected where serum samples are taken periodically and assayed for antidigoxin activity until a desired level of raised antibodies is achieved. The raised antibodies can then be evaluated for their specificity to digoxin and the extent of cross-reactivity with digoxin metabolites in the manner to be discussed with respect to the following Examples.

The antidigoxin antibodies, as isolated in the serum samples taken from the animal in which they are raised, can be used in an immunoassay diagnostic method to determine the concentration of native or pure digoxin in serum samples from humans and other animals in which it is desired to detect the presence of native digoxin. For example, radioimmunoassay in which the digoxin to be measured competes with a known amount of radiolabelled digoxin for binding to the antibody, or fluorescence polarization immunoassay in which the unknown digoxin competes with a known amount of a fluorescent digoxin derivative for binding to the antibody. It is appreciated that the antidigoxin antibodies may be purified and isolated from the serum and furthermore, it is possible to develop a hybridoma which produces a monoclonal antibody having the same specificity to the carbohydrate moiety of digoxin.

EXAMPLE 1

By reductive ozonolysis of digoxin, the compound of formula III is prepared. 128 μmoles digoxin (Sigma St. Louis, Mo.) was spiked with [12α $^3$H]-digoxin (NEN, Boston, Mass.) and dissolved in 3.5 ml $CH_2Cl_2$ MeOH (5:1 v/v). The solution was cooled to −78° C. in dry ice/acetone. Ozone (from a high voltage ozone generator) was bubbled through the solution (0.4 ml/min)in the presence of a starch iodine paper. After 5 min, the tube was capped and the reaction mixture stirred for 3 hours at −78° C. The reaction tube was then flushed with nitrogen and 2 ml of dimethyl sulfide (Sigma) was added. The mixture was stirred overnight in a Duwar flask and the temperature allowed to rise to 25° C. The product was evaporated under nitrogen.

The products of reductive ozonolysis of digoxin were separated by thin layer chromatography and visualized by a carbohydrate specific staining procedure. Little or no starting material remained and a new diffuse band of reduced mobility is detected, as shown in lane G of FIG. 1. Although the product gave a positive reaction with 2.4 dinitrobenzene indicating the presence of carbonyl group, NMR analysis of the reaction mixture, however, failed to show a significant signal for the aldehydic proton expected for the structure of formula III. This is due to the instability of the product of formula III, because the estro linkage is unstable and spontaneously looses the glyoxylate to form the compound of formula IV.

EXAMPLE 2

After the reductive ozonolysis of digoxin, in accordance with Example 1, the reaction mixture was immediately treated with 0.1M $KHCO_3$ for 3 hours at room temperature. The reaction mixture was separated by preparative high performance thin layer chromatography (ethylacetate:acetone 2:1 v/v). The product formed was scrapped and eluted and subjected to NMR and mass spectral analysis. The NMR spectra of the resulting derivative of formula IV and of native digoxin were compared as shown in FIGS. 2a and 2b, where FIG. 2a is the spectra of digoxin and FIG. 2b of the spectra of the compound of formula IV. Several features of the spectra demonstrate that the lactone ring has been modified. Firstly, the olefinic proton on C22 (FIG. 2) has been completely removed. Secondly, the quartet due to the methylene protons at C20 have moved upfield indicating a change in electronic environment, while the C18 methyl protons (but not the C19 methyl protons) have shifted downfield. The proton at C12 has shifted and the proton at C3 is also shifted downfield in the hydrolysed product. The changes in proton chemical shifts are given in the following Table 1.

TABLE 1

| | Change in Proton Chemical Shifts After Ozonolysis and Alkaline Hydrolysis | |
|---|---|---|
| Proton | Digoxin PPM | Compound IV PPM |
| C22 | 6.325 | — |

TABLE 1-continued

Change in Proton Chemical Shifts After Ozonolysis and Alkaline Hydrolysis

| Proton | Digoxin PPM | Compound IV PPM |
|---|---|---|
| anomeric* | 5.436 | 5.433 |
| (Cl' " """) | 5.410 | 5.407 |
| C21 | 5.338 | 4.941 |
|  | 5.287 | 4.487 |
|  | 5.193 | 4.751 |
|  | 5.142 | 4.702 |
| ** C3' " """ | 4.692 | 4.689 |
|  | 4.654 | 4.651 |
|  | 4.481 | 4.474 |
| C3, C12 | 3.812–3.741 | C3 3.966–3.914 |
|  |  | C12 3.736–3.693 |
| ** C4' " """ | 3.625 | 3.620 |
|  | 3.596 | 3.590 |
|  | 3.566 | 3.558 |
|  | 3.513 | 3.509 |
|  | 3.486 | 3.483 |
| C18 | 1.264 | 1.316 |
| C19 | 0.877 | 0.865 |

* The anomeric protons of the three sugars are superimposed to give a doublet with an approximate 8 Hz coupling.
** Small couplings on major peaks have been averaged.

The signals due to carbohydrate protons are superimposable before and after treatment. The 8 Hz coupling for the anomeric protons confirms the β linkage of the glycose moieties. Integration of the anomeric C1,3,4,5, and methyl protons of the sugar moieties shows no loss of carbohydrates has occurred during these reactions. Glycosidic cleavage would result in significant changes in the carbohydrate proton resonance, particularly C4. This was not found to occur as evidenced in FIG. 2 and Table 1.

Figure 3:
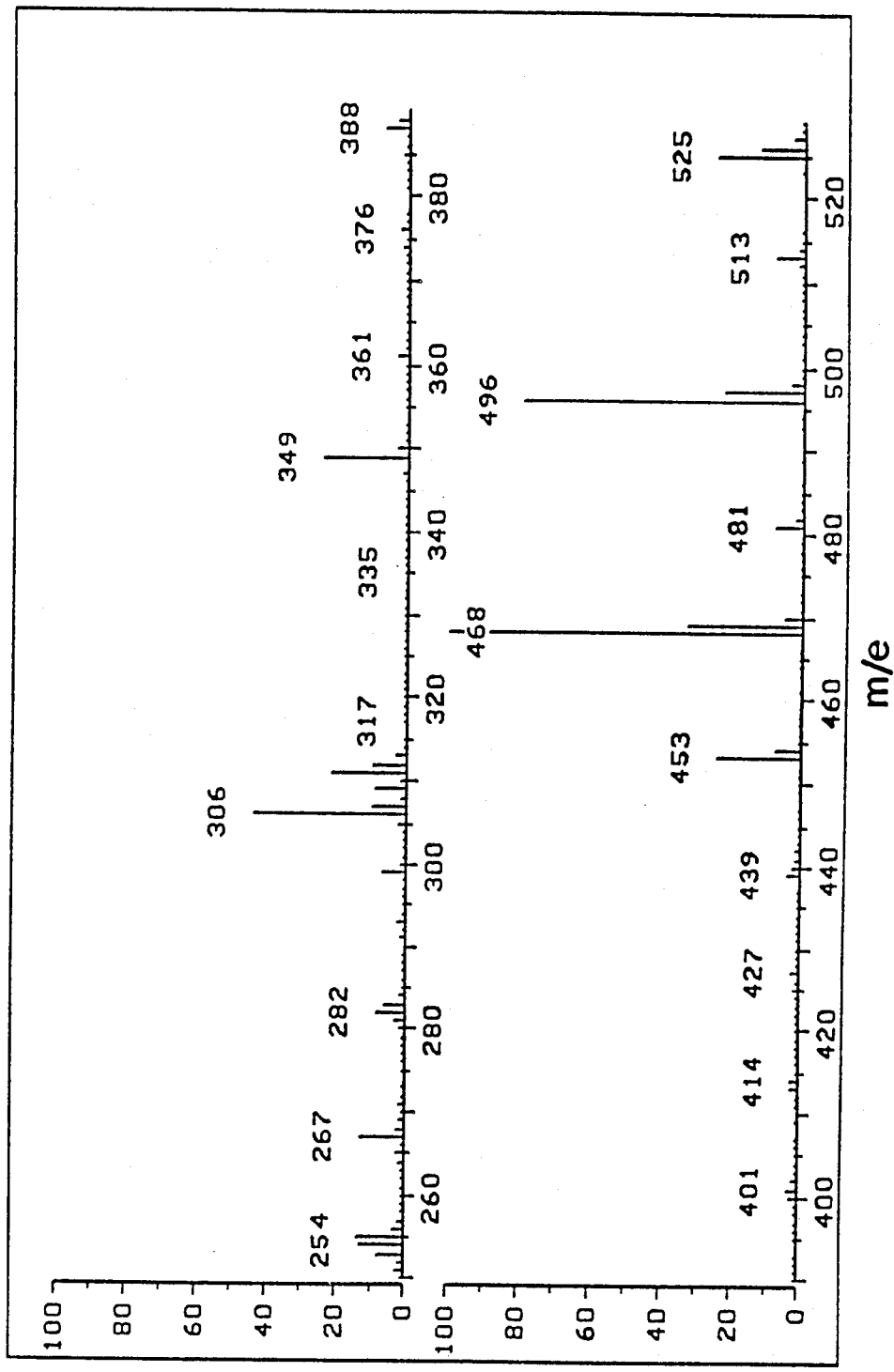
FIG. 3 shows the results of the mass spectrometer analysis of the hydrolized product of the digoxin derivative.

The compound of formula IV was also subjected to mass spectral analysis as shown in FIG. 3 after cleavage of the carbohydrate moiety and derivatization with heptafluorobutyrate (HFB). The aglycone of compound IV containing one HFB group should give an ion peak at 596. Cleavage of the C13-C17 and C14-C-15 bonds should result in a peak at 496. Loss of HFB from this species should give a peak at 282, while loss of CO (C16) should give a 468 signal. Loss of HFB should give 254 or loss of $CH_3$ (C20) should account for the signal at 453m/e. Thus, the major peaks coincide with those predicted from the structure of formula IV.

The NMR and mass spectrametric analysis confirm the production of the compound of formula IV following ozonolysis and alkali hydrolysis of digoxin. This confirms the presence of the compound of formula III as the immediate product of the reductive ozonolysis of digoxin.

EXAMPLE 3

Due to the instability of the product of formula III, it was discovered that it could be stabilized by immediate reaction with a protein to provide the immediate formation of a Schiff's base with the aldehyde generated at C23 to stabilize the ester linkage between C23 and C21.

30 mg of mBSA was dissolved in 12.5 ml $CH_2Cl_2$:MeOH (1:1.5 v/v) and the pH adjusted to 11 using 0.1N NaOH. The viscous product obtained after reductive ozonolysis of Example 1 was immediately dissolved in this solution and the reaction mixture was stirred at room temperature overnight. 120 μmoles of sodium cyanoborohydride was added to the conjugation reaction and stirred for 4 hours at room temperature. The reaction mixture was dialysed vs water for 4 to 6 days. The dialysed conjugate was lyophilized or maintained at −20° C. in preparation for injection in the immunization technique.

Figure 4:
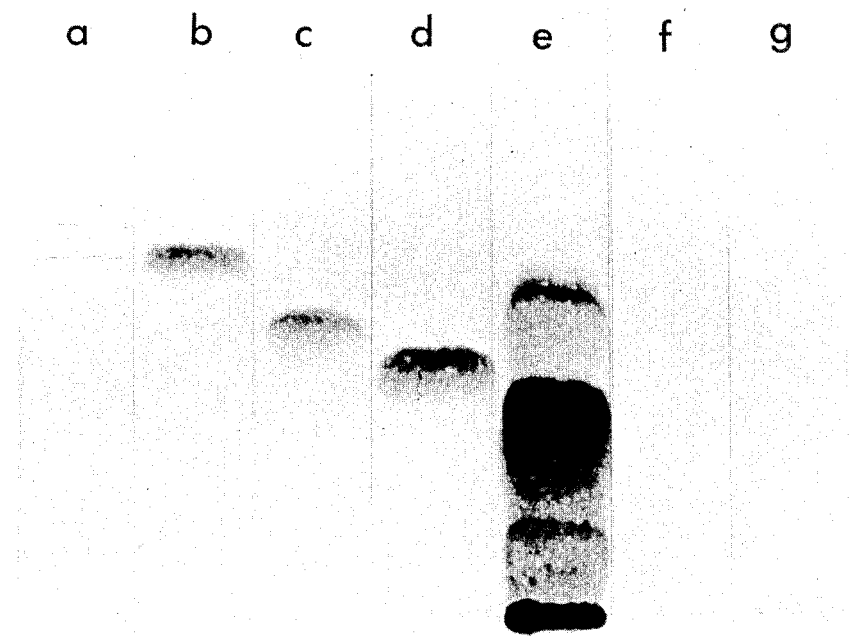
FIG. 4 shows the results of thin layered chromatography of the reaction mixture following protein conjugation.

Analysis of the reaction mixture by thin layer chromatography revealed a new carbohydrate containing species as shown in FIG. 4, lane E. The new carbohydrate moiety remains at the origin. Unconjugated mBSA runs at the thin layer chromatography origin but does not stain for carbohydrate, as shown in lane F of FIG. 4. The reaction mixture was extensively dialysed when the unconjugated steroid derivatives were removed as indicated in lane G of FIG. 4. The stoichemetry of the conjugate was calculated from the radioactivity from 3'H-digoxin incorporated into the conjugate. Between 40 and 50 digoxin molecules are coupled per mBSA molecule.

EXAMPLE 4

The conjugate of Example 3 (1 mg protein containing ~50 digoxin molecules/BSA) was dissolved in water, emulsified in an equal volume of Freunds complete adjuvant, and injected subcutaneously into a rabbit at multiple sites. A booster injection of the same conjugate (1.5 mg protein) in incomplete adjuvant was administered after one month. A second booster using a less potent conjugate (5.8 mg protein containing - 5 digoxin molecules/BSA) was given three weeks later. Serum samples were taken periodically and assayed for antidigoxin activity undiluted prior to the second booster and diluted 1 in 10 thereafter.

Figure 5:
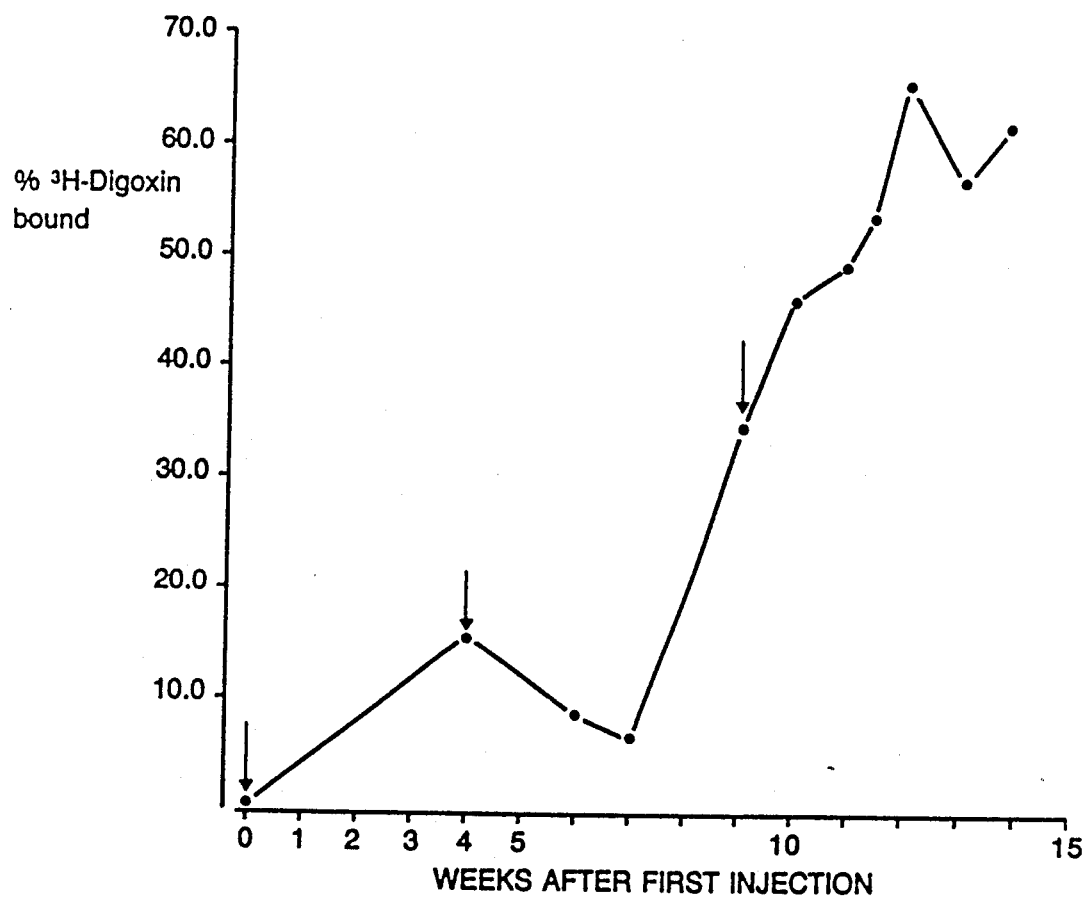
FIG. 5 is a graph plotting the immunization schedule.

Antidigoxin activity was detected approximately eight weeks after subcutaneous injection of the mBSA/digoxin derivative conjugate, as shown in FIG. 5. Serum samples up to this time were assayed undiluted and thereafter at a 1 in 10 dilution.

EXAMPLE 5

The $^3$H-digoxin radioimmunoassay method was adapted from that previously described in Cerceo E. and Elloso CA (1972) Factors Affecting the Radioimmunoassay of Digoxin, *Clin. Chem.* 18, 539–542. Briefly, tubes containing 0–30 ng $^3$H-digoxin (3000 dpm) in PBS were incubated at room temperature for 15 mins in the presence of 1/20 diluted antidigoxin serum. Ice cold dextran coated charcoal was added and incubated at 4° C. for 10 mins. This mixture was centrifuged and the $^3$H-digoxin remaining in the supernate was counted in a liquid scintillation spectrometer. Controls in the absence of serum and for non-immune serum were performed in parallel.

EXAMPLE 6

Multiwell ELISA plates were coated with 500 ng/well digoxin/BSA conjugate or BSA alone. Serial dilutions of immune vs non-immune serum were assayed for antigen binding using a goat anti rabbit Ig/horseradish peroxidase conjugate. Binding was quantitated using a Dynatech automatic ELISA reader.

EXAMPLE 7

Antidigoxin antibodies raised against BSA periodate conjugated digoxin were purchased from Antibodies Incorporated (Davis, Calif.) and Wien Laboratories (Succasunna, N.J.). Antidigoxin activity was determined using the $^{125}$I-digoxin radioimmune assay as previously described. Soldin, S; Papanastasion-Diamand, A; Heyes, J;, Lingwood C. A. and Olley, P. (1984) *Are Immunoassays for Digoxin Reliable? Clin. Biochem.* 17, 317–320. The immune serum was precipitated with 40% ammonium sulfate. The precipitate was redissolved and dialysed against phosphate buffered saline pH 7.4 (PBS). Antidigoxin antibodies were further purified by immunoaffinity chromatography. Digoxin was covalently linked to agarose by use of a photoactive heterobifunctional crosslinking agent as described in Lingwood, C. A. (1984) *Production of Glycolipid Affinity Matrices by Use of Heterobifunctional Crosslinking Agents, J. Lipid Res.* 25, 1010–1012. Amino hexyl agarose was treated with 2 mM hydroxysuccinimidyl azidobenzoate in the dark for 1 hour at room temperature. The beads were washed with water and 2 mg $^3$H-digoxin (1 mg/ml enthanol/water 1:1) was added. The beads were rotoevaporated to dryness when the digoxin was absorbed onto the beads. The dry beads were then irradiated for 2 min/1 cm from a Mineralight II UV source with stirring, when the digoxin is covalently attached to the agarose beads. The matrix was washed with 100 column volumes 50% ethanol and 50 column volumes water. The wash fractions were concentrated and unbound $^3$H-digoxin was measured. The amount of digoxin coupled/ml agarose was calculated (0.2 $\mu$moles/ml beads).

The immunoglobulin fraction from 1 ml immune serum was applied and the digoxin column was washed with PBS. Antidigoxin activity was measured using the automated $^{125}$I-RIA method. All antidigoxin activity was found to bind to the column. Specific antibodies were eluted by addition of 10 ml 1M KI followed by 10 ml 1M KSCN. The eluted fractions were dialysed, concentrated vs sucrose, dialysed and used in the RIA.

Cross-reactivity of commercial antidigoxin antibodies towards the digoxin metabolites in which one, two and three sugars have been removed (digoxigenin bisdigitoxoside, monodigitoxoside and dihydrodigoxigenin respectively) was measured. The results shown in Table 2 demonstrate that the carbohydrate metabolites of digoxin are approximately 3 to 4 fold more immunoreactive than native digoxin in the standard assay for digoxin. Purification of the antidigoxin antibodies by affinity chromatography considerably reduces this cross reactivity such that the metabolites are now recognized on a one to one basis relative to digoxin.

TABLE 2

Comparison of the Cross Reactivity of Digoxin Glycosidic Metabolites in the Standard RIA* For Digoxin

| Antigen | True Concentration (nmoles/l) | Concentration Measured by RIA Using | |
|---|---|---|---|
| | | whole Serum | Affinity Purified** Antibody |
| Digoxigenin | 7.2 | 25.2 | 6.9 |
| Digoxigenin bisdigitoxide | 6.3 | 25.2 | 6.3 |
| Digoxigenin monodigitoxide | 7.5 | 24.3 | 5.0 |
| Dihydrodigoxigenin | 8.3 | 0.8 | 0.8 |

*$^{125}$I-digoxin RIA as previously described using commercial antidigoxin antibodies.
**Affinity purified from the same immune serum Antidigoxin activity was detected approximately eight weeks after subcutaneous injection of the mBSA/-digoxin derivative conjugate, as shown in FIG. 5. Serum samples, in accordance with Example 4, up to this time were assayed undiluted and thereafter at a 1 to 10 dilution. In accordance with the procedure of Example 5, the $^3$H-digoxin radioimmunoassay the percentage digoxin bound was constant up to a dilution of 1 to 40. However, considerably greater reactivity was demonstrated in the enzyme linked immunosorbent assay of Example 6 as shown in FIGS. 6a and 6b.

The coding for the results shown in FIGS. 6a and 6b are as follows:
- ▲ Immune serum vs Digoxin/BSA conjugate
- ● Immune serum vs BSA
- ◤ Nonimmune serum vs Digoxin/BSA
- ■ Nonimmune serum vs BSA The binding of antidigoxin antibodies to a BSA/-digoxin conjugate prepared by reductive ozonolysis is shown in FIG. 6a, whereas the binding of the antibodies to the conjugate prepared by periodate oxidation of digoxin is shown in FIG. 6b.

Preferential binding to the mBSA/digoxin derivative conjugate, in which the carbohydrate moiety was preserved intact, was observed in FIG. 6a, as compared to FIG. 6b. Using this assay, activity above background could be detected for the immune serum at a dilution of 1 in $10^8$ indicating a potent antibody activity.

EXAMPLE 8

Figure 7B:
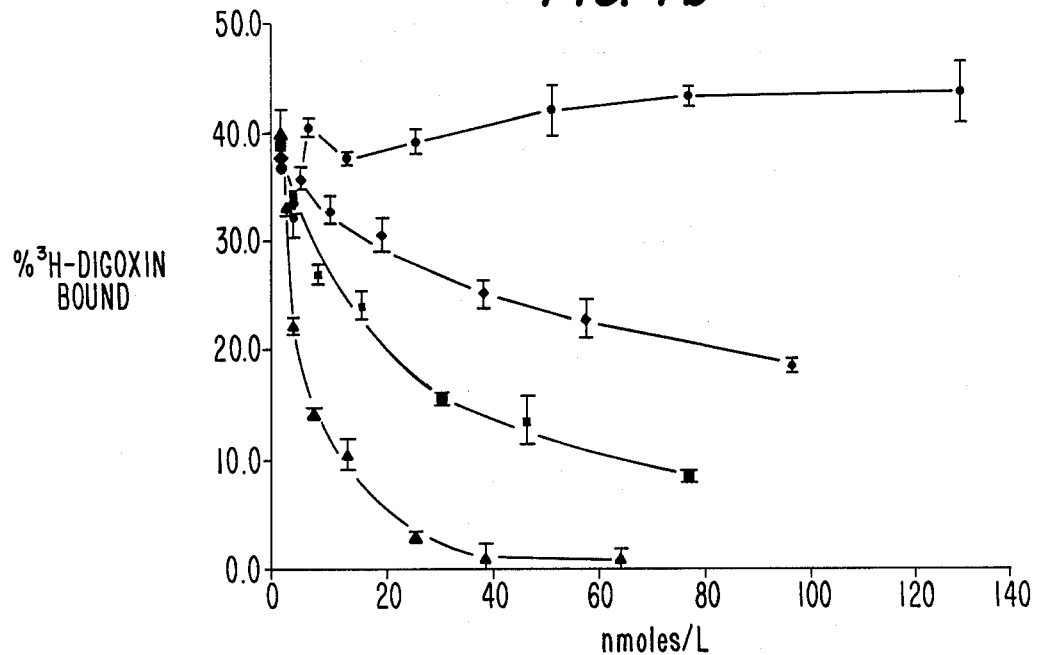
Figure 7B:
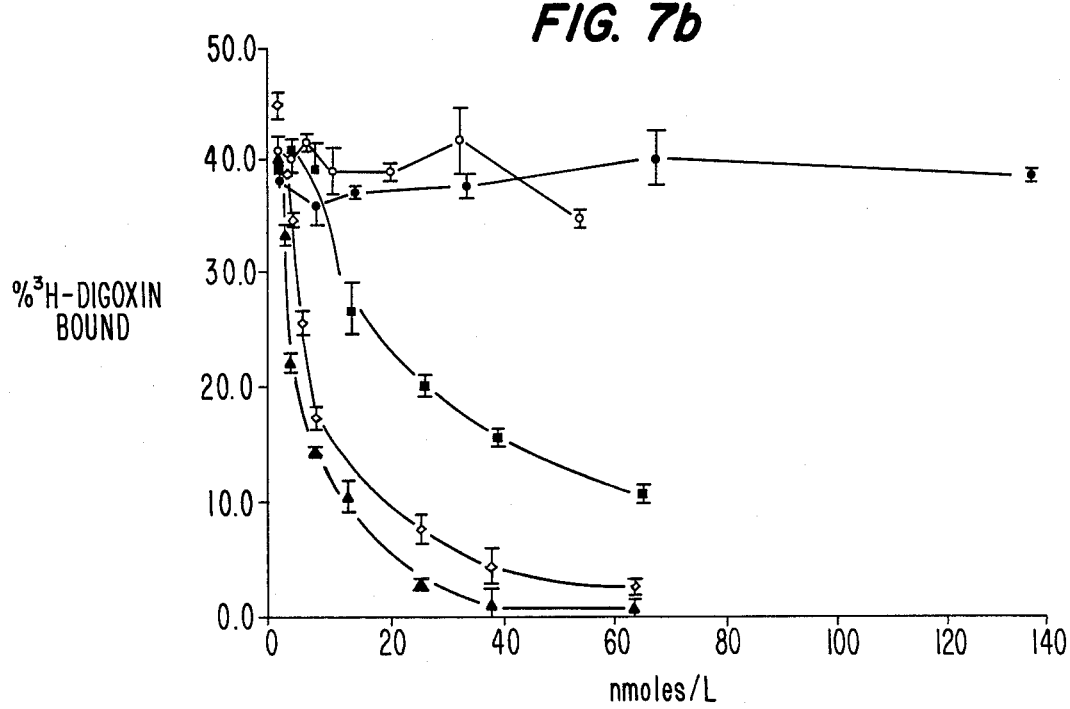

The specificity of antidigoxin serum was evaluated and the results shown in FIGS. 7a and 7b.

The coding for the results shown in FIGS. 7a and 7b are as follows:

(A)
- ▲ digoxin
- ■ digoxigenin bisdigitoxide
- ◆ digoxigenin monodititoxide
- ● digoxigenin (B)
- ▲ digoxin
- ◆ digitoxin  dihydrodigoxin
- ● digitoxose  ● deslanoside The degree of cross reactivity of the digoxin metabolites was monitored using the $^3$H-digoxin radioimmunoassay. The binding of $^3$H-digoxin was effectively competed out in the presence of unlabelled digoxin to give the standard curve shown in FIG. 7a. The bisdigitoxoside was a considerably less potent inhibitor, showing a cross-reactivity index of 14.6% (calculated from the molar concentration required to reduce the $^3$H-digoxin binding by 50%), and the reactivity of the monodigitoxoside is further reduced (cross reactivity index 3.7%). The agylcone digoxigenin was found to be an ineffective antigen for the new antibody. The free digitoxose sugar does not compete for digoxin binding and digitoxin shows a cross reactivity index of 11% (FIG. 7b).

EXAMPLE 9

A comparison was made between the antiserum of Example 4 and the commercially available antidigoxin serum using FPIA (fluorescence polarization immuno assay) to measure the digoxin concentration for solutions containing known levels of the digoxin metabolites as identified in the following Table 3.

TABLE 3

Cross Reactivity of Digoxin Metabolites

| | Conc. nmol/l | | |
|---|---|---|---|
| | | Digoxin Apparent value measured by | |
| Metabolite | Actual$^a$ | [$^3$H]digoxin RIA$^b$ | FPIA$^c$ |
| (actual)$^a$ | | | |
| Digoxigenin | 10.2 | 0 | 0 | 13.8 |
| Monodigitoxide | 7.7 | 0 | 0.7 | 10 |

TABLE 3-continued

| | Cross Reactivity of Digoxin Metabolites | | |
|---|---|---|---|
| | | Conc. nmol/l | |
| | | Digoxin Apparent value measured by | |
| Metabolite (actual)[a] | Actual[a] | [$^3$H]digoxin RIA[b] | FPIA[c] |
| Bisdigitoxide | 6.1 | 0 | 0.8 | 6.05 |
| Digitoxin | 10.5 | 0 | 0 | 9.6 |
| Digoxigenin monodigitoxide bisdigitoxide and dihydrodigoxin | a mixture of 0.64 2.56[d] of each of the metabolites | | 2.56 | 5.2 |

[a] diluted from a stock prepared by weighing
[b] with antibodies raised against ozonized digoxin-BSA
[c] with antibodies generated against periodate-oxidized digoxin-BSA conjugate and assayed by fluorescence polarization immunoassay
[d] standard digoxin measured in the presence of metabolites Only the carbohydrate specific antidigoxin antibody of this invention was able to distinguish the metabolites from the native digoxin.

The narrow range for therapeutic, as opposed to toxic dose, makes digoxin one of the more difficult drugs to administer particularly in infants. As discussed, the metabolism of digoxin results in metabolites which vary greatly in their cardiac efficacy, toxicity and renal clearance. This problem is compounded by considerable individual differences in digoxin metabolism, absorption and cases of impaired renal function. These factors necessitate an accurate means for monitoring serum digoxin levels. As demonstrated in Table 1, the existing procedure cannot distinguish between digoxin and several of its metabolites in an accurate reliable manner. The concentration of metabolites of digoxin, as shown in Table 1 and the standard sample were overestimated by up to four fold by using commercially available anti-serum.

According to a preferred embodiment of this invention, the discovery that, by the use of organic soluble methylated BSA, which is immediately reacted with the produced aldehyde of the digoxin derivative, results in a conjugate which raises antibodies specific to the unique carbohydrate moiety of digoxin. As shown in FIG. 7a, by use of the mBSA/digoxin derivative conjugate of this invention, a high titer activity ($1 \times 10^8$) was obtained. Minimal activity against unconjugated BSA was observed. When the antibody activity was measured using a BSA-digoxin prepared by the periodate oxidation of the terminal sugar, reactivity was only marginally greater than that observed for BSA alone, as shown in FIG. 6b, again suggesting that the antibody recognizes the carbohydrate chain. As shown in FIG. 7a, sequential removal of the glycose units of the carbohydrate moiety of digoxin reduces the antigenic reactivity of the antibody. The free, digitoxose, does not cross react at all with the antibody shown in FIG. 7b, suggesting a requirement for the steroid moiety. The digoxin analogue, digitoxin, in which the hydroxyl group at C12 of the steroid is missing, shows considerable reduced reactivity, although the carbohydrate chain is unaltered. This indicates that the conjugate of mBSA at the C23 position is sufficiently far from C12 to permit immune recognition at this site.

Although preferred embodiments of the invention have been described in detail, it will be understood by those skilled in the art that variations may be made thereto without departing from the spirit of the invention or the scope of the appended claims.

The embodiments of the invention in which an exclusive property or privilege is claimed are defined as follows:

1. A digoxin derivative/immunogenic protein conjugate, said digoxin derivative having a lactone ring at C17 of digoxin opened at a double bond between C20 and C23 of said lactone ring, said digoxin derivative having the same carbohydrate moiety as digoxin, said immunogenic protein being coupled to the C23 of said opened lactone ring without altering said carbohydrate.

2. A conjugate of claim 1, wherein said immunogenic protein is bovine serum albumin.

3. A conjugate of claim 1, wherein said immunogenic protein is methylated bovine serum albumin.

4. A conjugate of claim 1, wherein said digoxin derivative is coupled to several amine sites on said protein.

5. A conjugate of claim 1, wherein a diamine links said C23 of said opened lactone ring to said protein in coupling said protein to said digoxin derivative.

6. A conjugate of claim 5, wherein said diamine is 4-aminophenylethylamine.

7. A conjugate of claim 1, wherein said digoxin derivative is 3β,12β,14β-trihydroxy-5β,17β (glyoxylate ester of $C_{21}$hydroxy, $C_{20}$keto)etianic acid 3-tridigitoxoside.

8. A process for preparing a digoxin derivative/immunogenic protein conjugate comprising opening the double bond between C20 and C23 of the C17 lactone ring of digoxin having a carbohydrate moiety at the C3 of the digoxin molecule, and coupling an immunogenic protein to the C23 of the resultant opened lactone ring without altering said carbohydrate moiety.

9. A process of claim 8, wherein said double bond between C20 and C23 is opened by oxidizing said lactone ring with $O_3$ to produce an ozonide and reducing said ozonide to open said ozonide to produce a C23 aldehyde.

10. A process of claim 9, wherein said immunogenic protein is reacted immediately with said C23 aldehyde.

11. A process of claim 10, wherein the oxidation and reduction steps are carried out in an organic medium, coupling methylated bovine serum albumin which is soluble in said organic medium immediately with said C23 aldehyde of said digoxin derivative.

12. A process of claim 11, wherein a plurality of molecules of digoxin derivatives are coupled to a methylated bovine serum albumin molecule and reducing each double bond coupling at C23 to produce a stable digoxin derivative/methylated bovine serum albumin conjugate, separating said conjugate from said organic medium.

13. A process of claim 12, wherein said ozonide is reduced with dimethyl sulfide.

14. A process of claim 12, wherein cyanoborohydride is used to reduce each double bond coupling at C23.

15. A process of claim 12, 13 or 14, wherein approximately 30 to 50 digoxin derivatives are coupled to a single methylated bovine serum albumin molecule.

16. A process of claim 12, wherein said prepared conjugate is lyophilized.

17. A process of claim 16, wherein said conjugate in a reaction medium is dialysed prior to lyophilization.

18. An antidigoxin antibody specific to said digoxin derivative/immunogenic protein conjugate of claim 1.

19. An antidigoxin antibody specific to said digoxin derivative/immunogenic protein conjugate of claim 2.

20. An antidigoxin antibody specific to said digoxin derivative/immunogenic protein conjugate of claim 3.

21. An antidigoxin antibody specific to said digoxin derivative/immunogenic protein conjugate of claim 4.

22. An antidigoxin antibody specific to said digoxin derivative/immunogenic protein conjugate of claim 7.

23. An antidigoxin antibody specific to said digoxin derivative/methylated bovine serum albumin prepared in accordance with claim 11.

24. An antidigoxin antibody specific to said digoxin derivative/methylated bovine serum albumin prepared in accordance with claim 12.

25. An antidigoxin antibody specific to said digoxin derivative/methylated bovine serum albumin prepared in accordance with claim 13.

26. An antidigoxin antibody specific to said digoxin derivative/methylated bovine serum albumin prepared in accordance with claim 14.

27. An immunoassay diagnostic method for detecting the presence of digoxin in a fluid sample comprising contacting the fluid sample with the antidigoxin antibody of claim 18, 19 or 20 so as to form an antidigoxin antibody - digoxin immune complex.

28. An immunoassay diagnostic method for detecting the presence of digoxin in a fluid sample comprising contacting the fluid sample with the antidigoxin antibody of claim 21, 22 or 23 so as to form an antidigoxin antibody - digoxin immune complex.

29. An immunoassay diagnostic method for detecting the presence of digoxin in a fluid sample comprising contacting the fluid sample with the antidigoxin antibody of claim 24, 25 or 26 so as to form an antidigoxin antibody - digoxin immune complex.

* * * * *